United States Patent [19]

Outinen et al.

[11] Patent Number: 5,547,687
[45] Date of Patent: Aug. 20, 1996

[54] METHOD FOR REMOVING PHENYLALANINE FROM PROTEINACEOUS COMPOSITIONS, A PRODUCT SO OBTAINED AND USE THEREOF

[75] Inventors: Marko T. Outinen, Espoo; Olli Tossavainen, Helsinki; Matti Harju, Nummela; Pekka Linko, Espoo, all of Finland

[73] Assignee: Valio Oy, Helsinki, Finland

[21] Appl. No.: 295,784

[22] PCT Filed: Mar. 10, 1993

[86] PCT No.: PCT/FI93/00086

§ 371 Date: Sep. 12, 1994

§ 102(e) Date: Sep. 12, 1994

[87] PCT Pub. No.: WO93/17581

PCT Pub. Date: Sep. 16, 1993

[30] Foreign Application Priority Data

Mar. 13, 1992 [FI] Finland ................................ 921097

[51] Int. Cl.⁶ .................................................. A23L 1/305
[52] U.S. Cl. ................................................. 426/2; 426/656
[58] Field of Search ................................. 426/656, 2

[56] References Cited

U.S. PATENT DOCUMENTS

| | | |
|---|---|---|
| 4,016,147 | 4/1977 | Fujimaki et al. . |
| 4,293,571 | 10/1981 | Olofsson et al. . |
| 4,384,136 | 5/1983 | Steinmetzer . |
| 5,242,697 | 9/1993 | Luca .................... 426/656 |
| 5,393,532 | 2/1995 | Wachtel ............... 426/656 |
| 5,411,757 | 5/1995 | Buist .................... 426/656 |

FOREIGN PATENT DOCUMENTS

| | | |
|---|---|---|
| 151442 | 8/1981 | Denmark . |
| 169935 | 8/1987 | Denmark . |
| 2487642 | 7/1980 | France . |
| 2319581 | 4/1973 | Germany . |
| 3049328A1 | 12/1979 | Germany . |
| 147615 | 4/1981 | Germany . |
| 283256A7 | 7/1988 | Germany . |
| 921097 | 5/1993 | Germany . |
| WO87/03785 | 7/1987 | WIPO . |

OTHER PUBLICATIONS

"Adsorption Chromatography of Phenylalanine", Biotechnology and Bioengineering, vol. 33, pp. 1324–1329 (1989).
"A Low-Phenylalanine, High-Tyrosine Plastein As an Acceptable Dietetic Food. Method of Preparation by Use of Enzymatic Protein Hydrolysis and Resynthesis", vol. 41 (1976)–Journal of Food Science.
"Enzymatic Production of a Low-Phenylalanine Product From Skim Milk Powder and Caseinate", 938, Journal of Food Science, vol. 56, No. 4, 1991.
Journal of Food Science, vol. 56, No. 4, 1991.
Derwent Publication 22698.
Derwent Publication 13419.
Search Report.
Our Response to Search Report.
Response dated Mar. 4, 1994 to the Written Opinion.

*Primary Examiner*—Carolyn Paden
*Attorney, Agent, or Firm*—Finnegan, Henderson, Farabow, Garrett & Dunner

[57] ABSTRACT

A method for removing phenylalanine from proteinaceous compositions is disclosed wherein the protein contained in the proteinaceous composition is degraded enzymatically with a proteolytic enzyme into a protein hydrolysate. The protein hydrolysate thus obtained is treated with adsorption resin in a column that is eluted with water, the fraction wherefrom phenylalanine has been removed is recovered and salts are removed from the fraction thus recovered. Finally the recovered fraction is concentrated and dried. A palatable proteinaceous composition from which phenylalanine has been removed is also disclosed. This proteinaceous composition is used as a special nutrient preparation or a component of such in the diet of patients suffering from phenylketonuria.

16 Claims, 1 Drawing Sheet

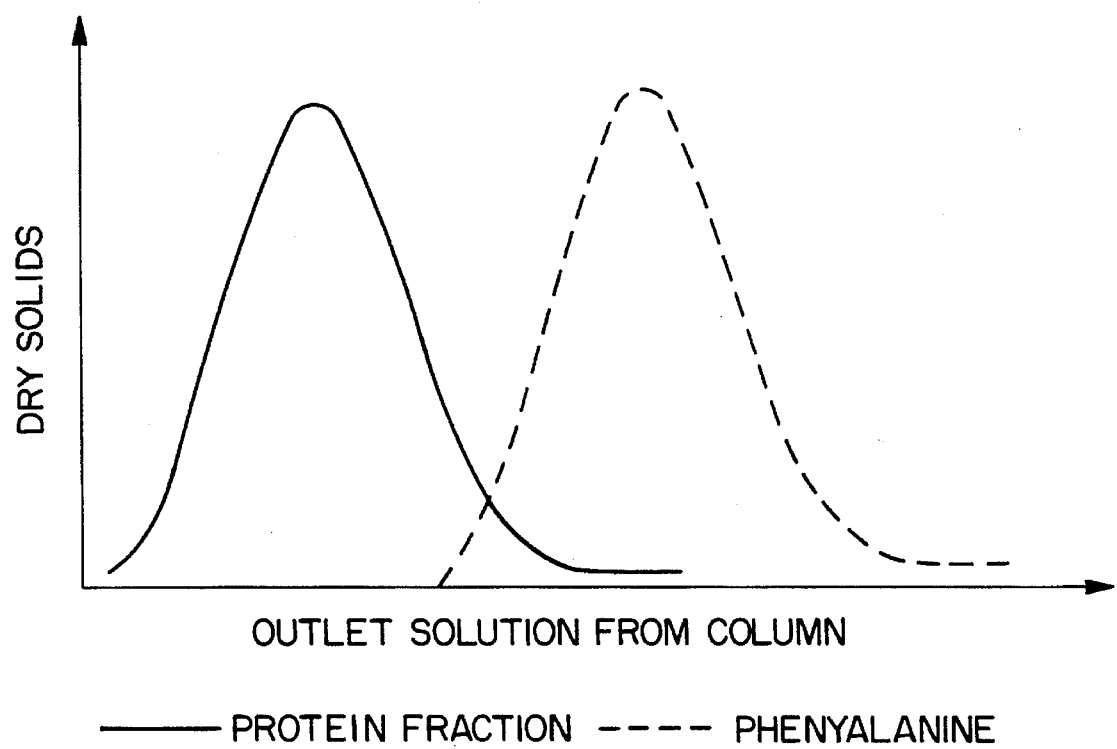

METHOD FOR REMOVING PHENYLALANINE FROM PROTEINACEOUS COMPOSITIONS, A PRODUCT SO OBTAINED AND USE THEREOF

BACKGROUND OF THE INVENTION

The present invention relates to a method for removing phenylalanine from proteinaceous compositions, yielding palatable, at least nearly phenylalanine-free protein hydrolysate compositions, a proteinaceous composition thus obtained wherefrom phenylalanine has been removed either totally or at least for the most part, and the use of such a substantially phenylalanine-free proteinaceous composition as a special nutrient product or a component of such, specifically in the diet of patients suffering from phenylketonuria (PKU).

The intake of phenylalanine from food cannot be diminished by selection of the protein source, since phenylalanine is present in all animal and vegetable proteins in an amount of about 4–6%. Thus the PKU patient is well advised to avoid foodstuffs rich in protein, such as egg, fish, meat and cheese. To satisfy the need for other essential amino acids, the patient should use clinical protein products wherefrom phenylalanine has been removed either totally or in part.

Phenylketonuria is a congenital disease that, if untreated, causes serious brain damage and often death within a few weeks from birth. The patient lacks the ability to produce phenylalanine hydroxylase (EC 1. 14.16.1) converting phenylalanine, an amino acid derived from food, to tyrosine. The accumulation of phenylalanine and its pyruvate, lactate and acetate derivatives in the blood and the spinal fluid causes compulsive movements, anaemia, skin roughening and finally brain damage. The disease can also be detected as an increased phenylacetylglutamine content in the patient's urine, wherefrom the disease has derived its name.

In the United States and most of Europe, one newborn in every 11 000–15 000 suffers from phenylketonuria. In Ireland, the disease is more common, one child in every 4 500 being a PKU patient. In Finland, phenylketonuria is very rare, and the proneness of newborns to phenylketonuria is not tested. In countries where PKU occurs, every child is tested within 1 –2 weeks from birth by monitoring the phenylalanine content in the blood. If the amount of phenylalanine in the blood is steadily on the increase, the treatment of the disease should be started three weeks from birth at the latest.

A strictly monitored diet is the only existing practical therapy. When the amount of phenylalanine derived from food can be maintained within certain limits, the phenylalanine content in the patient's blood will remain within allowable limits (20–40 mg/l). Tolerance against phenylalanine increases with age, and it has normally been possible to discontinue the diet at the age of about eight years. According to the most recent results of study, however, the diet should be continued longer, which places even higher requirements on the taste of the special nutrient product.

For the treatment of the disease, phenylalanine-free amino acid mixtures are prepared. Milk for the newborn baby is prepared from such "PKU protein" by adding the other necessary components, such as fat, water, lactose etc., to the protein. Also other ready-prepared PKU products may be produced from PKU protein by replacing the protein used in the production of the foodstuff by a phenylalanine-free amino acid mixture.

Such a commercial preparation is for instance the product PK AID III (manufacturer Scientific Hospital Supplies, England). Products of this kind, comprising substantially only free amino acids, have a bitter taste and may cause osmotic diarrhea. Thus the current recommendation is that the protein nitrogen supplement be derived from an enzymatic hydrolysate comprising oligopeptides, preferably dipeptides and tripeptides, which have been found to be better absorbed in the body than free amino acids (Silk, D. B. A. and Kochane, P. P. in *Clinical Nutrition* '81, London 1982. Ref. Kochane, P. P. and Silk, D. B. A. in Rombeau, J. L. and Caldwell, M. D., ed., *Enteral and tube feeding*.

Some methods for the removal of phenylalanine from proteins or proteinaceous compositions are already known. In the oldest of these known methods, the protein is first degraded into free amino acids with acid hydrolysis, whereafter the phenylalanine is removed from the mixture with active carbon (cf. for instance DD Patent 283 256). The drawback of this known method, however, is a poor yield, since generally not more than 50% of the amino acids are recovered while the remaining amino acids are adsorbed in the active carbon. Often also other hydrophobic amino acids are nearly totally adsorbed in the active carbon, as a result of which they must be subsequently added to the product. Further, the active carbon used as the adsorbent cannot be regenerated, which makes the method very expensive.

De Hollanda e Vasconcellos et al. set forth in *Biotechnology and Bioengineering* 56 (1989) pp. 1324–1329 a method wherein phenylalanine was removed from acid hydrolysate of casein with adsorption resin Amberlite XAD-4. With this method, it was possible to decrease the percentage of phenylalanine in the amino acids of the hydrolysate from 3.42% to 1.35%, which however is not a sufficiently low phenylalanine percentage to make the product suitable for use as a protein nitrogen supplement for PKU patients. The taste of the product was not commented on.

It has also been possible to remove phenylalanine from acid hydrolysate of protein by using a strong anion-exchange resin (U.S. Pat. No. 4 384 136 and British Patent 2 103 221 A). However, the anion exchange resin is not well suited to industrial production since it requires the use of buffer solutions.

Lopez-Bajoneron et al. set forth in *J. Food Sci.* 56(4) (1991) pp. 938–942 a method in which phenylalanine was removed from proteinaceous compositions. In the method, non-fat milk powder or caseinate was hydrolyzed first with protease produced by an Aspergillus oryzae strain and thereafter with papain. The hydrolysate was treated with a three-fold amount of active carbon as compared with the protein, and 92% of the phenylalanine was removed with a 50% protein yield.

Mockenberg et al. set forth in *Research in Food Science and Nutrition* 3 (1983) pp. 3–4 a method wherein acid hydrolysis was replaced by a two-step subtilisin-Pronase-enzyme hydrolysis the purpose of which was to liberate the C-terminal aromatic amino acids into free amino acids. However, the phenylalanine was not totally removed until an active carbon amount of 425% was used, and then 50% of the protein nitrogen was lost.

In the early 1970s in Japan, investigation on the possibilities of producing PKU protein by enzymatic methods was started. The object was to improve the taste and render the product more "protein-like". Several functional processes have indeed been developed on a laboratory scale [cf. Yamashita et al., *J. Food Sci.* 41 (1976) pp. 1029–1032; Fujimaki et al., U.S. Pat. No. 4 016 147; Mowlah et al., report, Technical Research Institute, Snow Brand Milk Products Co., Ltd., Japan (1985) pp. 29–39; Arai et al., *Agric. Biol Chem* 50 (1986) pp. 2929–2931; Owada et al., Advances in Neonatal Screening, Elsevier Science Publishers B.V., 1987, pp. 205–208; Maeda et al., *Agric. Biol. Chem.* 51 (1987) pp. 1501–1507]. However, the drawbacks of the processes include expensive special enzymes and the unsuitability of gel filtration to production scale.

In one two-step process included in the above methods, pepsin is first employed, with specific degradation of the raw material whey protein so that phenylalanine remains at the carboxy terminus of the peptide. The phenylalanine is further liberated into a free amino acid with carboxypeptidase or a commercial enzyme preparation having carboxypeptidase activity (for instance subtilisin, Pronase).

Further, in a one-step protein hydrolysis included in the above methods, an enzyme having both endopeptidase and exopeptidase activity is employed. Phenylalanine is separated from the mixture by gel chromatography.

The known methods for the removal of phenylalanine from proteinaceous compositions have so far not been satisfactory in view of industrial production. Hence there is a constant need for a method of removing phenylalanine from proteins or proteinaceous compositions that is practicable on an industrial scale and more cost-effective and productive than heretofore and also yields a substantially phenylalanine-free protein product having a better taste than heretofore.

SUMMARY OF THE INVENTION

Now a method has surprisingly been found wherewith the above problems can be eliminated and simultaneously a very palatable PKU protein hydrolysate of a physiologically high quality can be obtained with a good yield.

With the method of the invention, a substantially phenylalanine-free protein composition is obtained, being rich in nutritionally valuable dipeptides and tripeptides and containing only about 25% by weight of free amino acids. This product is very palatable and has no bitter taste. Further, it is readily soluble in hot water.

Furthermore, the method of the invention is well suitable for industrial production, and it comprises simple process units. The method has actually two steps. In the first step, the proteinaceous composition is enzymatically hydrolyzed, and in the second step the protein hydrolysate thus obtained is treated with adsorption resin. Further, the adsorption resin used in this method can be regenerated simply with lye commonly used in the foodstuff industry, and thus the resin is immediately ready for reuse. No impairment of the adsorption capacity of the resin has been found after several dozens of hydrolyzate batch—regeneration cycles.

Thus the invention relates to a method for removing phenylalanine from proteinaceous compositions, the method being characterized in that a) the protein contained in the proteinaceous composition is degraded enzymatically with a proteolytic enzyme into protein hydrolysate having a degree of hydrolysis of 30 to 60%, b) the protein hydrolysate thus obtained is ultrafiltered and the permeate is recovered, c) if desired, the pH of the solution is adjusted in the range pH 2–10 with an acid or base, d) the protein hydrolysate thus obtained is passed through a column filled with adsorption resin at a linear flow rate of 0.1–1.3 m/h at a temperature of 5°–65° C., e) the column is eluted with water at a linear flow rate 0.1–1.3 m/h, f) the fraction wherefrom phenylalanine has been removed is recovered, g) if necessary, salts are removed from the fraction that has been recovered, and h) finally, the recovered fraction is concentrated to a dry solids content of 70–80% by weight and, if desired, dried.

DESCRIPTION OF THE PREFERRED EMBODIMENTS

All animal and plant proteins have been found to contain about 4–6% by weight of phenylalanine on the total amount of protein.

In the first step of the process, the protein contained in the proteinaceous composition is degraded enzymatically with a proteolytic enzyme so as to give a degree of hydrolysis of about 30–60%.

The proteinaceous composition to be treated may be any proteinaceous composition containing other essential amino acids than phenylalanine as well, such as whey protein, casein or soy protein concentrate. In whey protein, the protein content may vary in the range 35–85% by weight. A typical protein content for soy protein concentrate is about 52% by weight.

The protein content of the starting material affects the protein content of the product. Since it is preferable for the product to contain as much protein as possible, the protein content in the starting material should be as high as possible, most preferably over 70% by weight.

Pancreatin is preferably used as the proteolytic enzyme, a suitable amount being about 3% by weight on the amount of protein.

In enzymatic treatment, the phenylalanine is liberated into free amino acids to an extent of approximately 70–90%. About 3.6–3.8% of the protein in the protein hydrolysate obtained is phenylalanine.

After the enzymatic hydrolysis, the protein hydrolysate is ultrafiltered to remove non-degraded protein and large-molecule peptides, and the permeate is recovered.

The recovered permeate is concentrated by evaporation to a dry solids content of 20–60% by weight. The concentrate thus obtained can be conveyed directly to further processing, or it can be stored at +5° C. prior to further processing. The concentrate having a dry solids content of 20–60% by weight can also be dried with a spray drier, if desired, before being processed further.

Prior to the adsorption resin treatment, the protein hydrolysate concentrate or powder is dissolved in hot water so as to give the solution a dry solids content of 20–30% by weight.

The adsorption resin treatment may be carried out at a pH of 2 to 10. If desired, the pH of the solution may be adjusted with a foodstuff-grade acid or base.

When a final product in the protein content of which not more than 0.5% is phenylalanine is aimed at, it is most advantageous to treat with resin a neutral solution having a pH of 6.5–7.0. Then no pH adjustment is needed subsequent to the hydrolysis step or removal of salt or salts from the product.

When a final product in the protein content of which not more than 0.1% is phenylalanine is aimed at, the resin must be treated with an acid solution having a pH of 3–4. The adsorption of phenylalanine from the solution into the resin is somewhat more efficient at a pH of 3–4 than at a neutral pH. Furthermore, the amino acid profile of the final product is even better with the use of said acid solution than with the use of a neutral solution (cf. Tables 1 to 3). The high tyrosine content of the final product as a result of the use of said acid solution deserves particular regard, since subsequent addition of tyrosine to the product is particularly difficult on account of its poor solubility. When an acid solution is used in the adsorption, removal of salt from the product solution either by electrodialysis or nanofiltration is necessary.

In the second step of the process, the protein hydrolysate is passed through a column filled with adsorption resin at a linear flow rate of 0.1–1.3 m/h. The adsorption process requires a certain minimum reaction time empirically determined to be sufficient, when the linear flow rate does not exceed 1.3 m/h. The adsorption improves with the use of slightly lower linear flow rates than this, but the time required by the process correspondingly increases, which increases the costs.

A hydrophobic polystyrene-based resin is preferably used as the adsorption resin. Suitable resins include Amberlite XAD 4 and Amberlite XAD 16, which are manufactured by Rohm & Haas (France).

The resin treatment can usually be carried out at a temperature of 5°–65° C., as the phenylalanine and phenylalanine-containing peptides are adsorbed into the resin at a pH of 2 to 10 and a temperature of 5° to 65° C. The most preferable resin treatment temperature is about 30° C., in which case no additional energy is needed for cooling or heating the solution.

The resin-filled column thus treated is eluted with water at the same flow rate at which the protein hydrolysate was conveyed into said column previously. The PKU protein is eluted from the column before the phenylalanine and the phenylalanine-containing peptides, so that the nearly phenylalanine-free fraction can be separated. FIG. 1 is a graphical illustration of the separation of the phenylalanine and the phenyl-alanine-containing peptides from the protein hydrolysate by means of an adsorption resin column.

If necessary, salts—such as excess chloride or sodium—are removed from the recovered nearly phenylalanine-free fraction for instance by electrodialysis.

Finally, the nearly phenylalanine-free product fraction is concentrated to a dry solids content of 70–80% by weight. If desired, the product fraction may be dried into a powder by freeze or spray drying.

The degree of removal of phenylalanine from the protein composition is about 92–100%. Thus, PKU protein having a phenylalanine content lower than that of the products prepared in the earlier methods based on the hydrolysis of protein (degree of removal of phenylalanine 90–95%) can be produced by the method. The total protein yield from the method is 45 to 65% according as how phenylalanine-free a product is desired. With a given removal ratio, the yield is at any rate better than in the methods disclosed in the literature.

The method may be realized either so that the resin treatment is carried out immediately after the hydrolysis step, or so that the resin treatment is carried out later.

The advantageousness of the method of the invention is enhanced by the fact that the adsorption resin used can be regenerated with 4% lye, whereafter the resin may be reused.

The amino acid profile of the substantially phenylalanine-free protein product obtained by the method of the invention is good in regard to the essential amino acids (Table 1). Only tyrosine and methionine additions are necessary. The product is rich in nutritionally valuable dipeptides and tripeptides and comprises about 25% of free amino acids. The taste of the product is excellent compared with the products on the market. Furthermore, the powder is readily soluble in hot water.

Thus, the invention further relates to a proteinaceous composition from which phenylalanine has been removed either totally or at least for the most part and which has been prepared by the method of the invention. This composition can be used as a special nutrient preparation or in the production of a special nutrient preparation.

The invention further relates to the use of the substantially phenylalanine-free proteinaceous composition thus obtained as a special nutrient preparation or a component thereof.

In the following examples, the invention will be described in closer detail.

EXAMPLE 1

100 kg of whey protein concentrate containing 35–90% by weight of protein (Kuivamaito Oy, Lapinlahti) was dissolved in 1900 l of hot water (5% solution as regards dry solids). The solution was heated with continuous stirring for 20 minutes at 65° C. to eliminate contaminants. The solution was cooled to 50° C. and the pH adjusted to 8.5 with 5M $Ca(OH)_2$. 3% by weight of pancreatin on the amount of protein was added, and hydrolyzation was performed for 6 hours. The pH was allowed to drop to 7.0, at which value it was maintained with 5M $Ca(OH)_2$. After the hydrolysis, the solution was pasteurized (95° C., 5 min.), cooled and ultrafiltered at 40° C. with cut-off 20 000 membranes. The permeate was recovered and concentrated by evaporation to a dry solids content of about 50%.

The concentrated protein hydrolysate was dried into a powder by spray drying.

EXAMPLE 2

The procedure of Example 1 was followed, but instead of drying, the permeate concentrated to a dry solids content of 50% was stored at 5° C. for further measures.

The total yield from the method was better than in Example 1, since the loss caused by the spray-drying of the hydrolysate was avoided.

EXAMPLE 3

12.5 g of a protein hydrolysate powder prepared in accordance with Example 1 was dissolved in 37.5 $cm^3$ of 80°–90° C. water. The pH of the protein hydrolysate solution was about 6.5–7.0, and thus no pH adjustment was needed at this stage. The solution that contained 25% by weight of dry solids, whereof about 70% was protein, was pumped at 30° C. into a 180 $cm^3$ XAD-4 adsorption resin column at a volumetric flow rate of 60 $cm^3$/h, which corresponded to a linear flow rate of 0.3 m/h. After the feeding of the protein hydrolysate solution batch, the column was eluted with water at the same flow rate.

The protein yield was about 50%. About 0.5% of the protein in the product fraction was phenylalanine.

EXAMPLE 4

7.5 g of a protein hydrolysate powder prepared in accordance with Example 1 was dissolved in 30 $cm^3$ of 80°–90° C. water. The 20% solution (pH 6.5–7.0) was pumped into a 180 cm³ XAD-16 adsorption resin column at a linear flow rate of 0.9 m/h at a temperature of 30° C. After the feeding of the protein hydrolysate solution batch, the column was eluted with water at the same flow rate.

The protein yield was about 50% and the dry solids yield about 55%. About 0.4% of the protein in the product fraction was phenylalanine.

EXAMPLE 5

The procedure of Example 4 was followed, except that the temperature was 65° C. Increasing the temperature improved the microbiological preservation of the resin column but increased the energy costs and possibly diminished the service life of the resin. The quality and yield of the product remained the same.

EXAMPLE 6

The procedure of Example 4 was followed, except that the temperature was 5° C. Lowering the temperature improved the microbiological preservation of the resin column but increased the energy costs. The quality and yield of the product remained the same.

EXAMPLE 7

2.1 kg of a protein hydrolysate powder prepared in accordance with Example 1 was dissolved in 10.5 l of 80°–90° C. water. The 20% solution (pH 6.5–7.0) was pumped into a 50 l XAD-16 adsorption resin column at a linear flow rate of 1.3 m/h at a temperature of 55 ° C. After the feeding of the protein hydrolysate solution batch the column was eluted at the same flow rate.

With a protein yield of 50%, about 0.3% of the amount of protein was phenylalanine; with a yield of a fraction was obtained that contained no phenylalanine. Data on the composition of the product fraction (with a 50% protein yield) are set forth in Tables 1 and 2.

TABLE 1

Amino acid composition of spray-dried PKU protein hydrolysate prepared in accordance with Example 7

| Amino acid | mg/g | % |
| --- | --- | --- |
| Asp | 88.4 | 12.6 |
| Thr | 49.41 | 7.0 |
| Ser | 37.87 | 5.4 |
| Glu | 156.38 | 22.3 |
| Gly | 11.01 | 1.6 |
| Ala | 36.64 | 5.2 |
| Val | 45.7 | 6.5 |
| Cys | 12.07 | 1.7 |
| Met | 12.63 | 1.8 |
| Ile | 31 | 4.4 |
| Leu | 57.95 | 8.3 |
| Tyr | 20.65 | 2.9 |
| Phe | 2.37 | 0.3 |
| Lys | 90.96 | 13.0 |
| His | 12.92 | 1.8 |
| Arg | 18.36 | 2.6 |
| Pro | 16.87 | 2.4 |
| Trp | + | + |
| Total | 701.19 | 100 |

TABLE 2

Composition of spray-dried PKU protein hydrolysate prepared in accordance with Example 7

| | |
| --- | --- |
| Protein | 66.0% |
| Ash | 6.0% |
| Water | 4.4% |
| Lactose | 12.1% |
| Sodium | 12.7 g/one kg of protein |
| Potassium | 26.1 g/one kg of protein |
| Calcium | 5.8 g/one kg of protein |
| Chloride | 6.1 g/one kg of protein |
| Phosphorus | 3.2 g/one kg of protein |

EXAMPLE 8

4.2 kg of a protein hydrolysate concentrate prepared in accordance with Example 2 was measured in 6.3 kg of water. The solution obtained, which had a dry solids content of 20% by weight and a pH of 6.7, was pumped into a 50 l XAD-16 adsorption resin column at a linear flow rate of 1.3 m/h at a temperature of 55° C. After the feeding of the protein hydrolysate solution batch, the column was eluted with water at the same flow rate.

The protein yield was about 50% and the dry solids yield about 55%. About 0.3% of the protein in the product fraction was phenylalanine.

EXAMPLE 9

22 g of a protein hydrolysate powder prepared in accordance with Example 1 was dissolved in 88 cm³ of 80°–90° C. water. The pH of the solution was adjusted with 30% HCl to 3.5, and the solution was pumped into a 180 cm³ XAD-16 adsorption resin column at a linear flow rate of 0.9 m/h at a temperature of 65° C. After the feeding of the protein hydrolysate solution batch, the column was eluted with water at the same flow rate.

The protein yield was about 52%. About 0.1% of the protein of the product fraction was phenylalanine.

To remove excess chloride, the product solution was electrodialysed, whereafter it was dried by spray drying.

EXAMPLE 10

22 g of a protein hydrolysate powder prepared in accordance with Example 1 was dissolved in 88 cm³ of 80°–90° water. The pH of the solution was adjusted with 30% HCl to 3.5, and the solution was pumped into a 180 cm³ XAD-16 adsorption resin column at a linear flow rate of 0.7 m/h at a temperature of 65° C. After the feeding of the protein hydrolysate solution batch the column was eluted with water at the same flow rate.

The protein yield was about 52%. About 0.07% of the protein of the product fraction was phenylalanine.

To remove excess chloride, the product solution was electrodialysed and concentrated by evaporation to have a dry solids content of about 50%. The composition of the concentrate is shown in Table 3.

TABLE 3

Composition of concentrated PKU hydrolysate prepared in accordance with Example 9

| | | |
| --- | --- | --- |
| Dry solids | 45.6 | % |
| Protein | 33.9 | % |

TABLE 3-continued

Composition of concentrated PKU
hydrolysate prepared in accordance with Example 9

| Lactose | 7.9 | % |
|---|---|---|
| Fat | <0.02 | % |
| Ash | 0.75 | % |
| Sodium (Na) | 1900 | mg/kg |
| Potassium (K) | 245 | mg/kg |
| Chloride (Cl⁻) | | |
| Magnesium (Mg) | 200 | mg/kg |
| Calcium (Ca) | 850 | mg/kg |
| Phosphorus (P) | 115 | mg/kg |
| Amino acids | | |
| Asp | 9.41 | % |
| Thr | 6.51 | % |
| Ser | 3.5 | % |
| Glu | 13.51 | % |
| Gly | 1.39 | % |
| Ala | 5.64 | % |
| Val | 8.2 | % |
| Cys | 1.16 | % |
| Met | 2.49 | % |
| Ile | 4.83 | % |
| Leu | 8.06 | % |
| Tyr | 3.98 | % |
| Phe | 0.07 | % |
| Lys | 20.65 | % |
| His | 3.1 | % |
| Arg | 6.75 | % |
| Pro | 0.75 | % |
| Trp | + | + |

EXAMPLE 11

A similar procedure was followed as in Example 4, except that the pH of the solution was raised to 10.0 with 10% NaOH prior to the resin treatment. Since the solution was strongly alkaline, it needed no intense heating treatment for clarification.

The protein yield was about 45%. 0.4% of the protein in the product solution was phenylalanine.

Excess sodium was removed from the solution by electrodialysis, whereafter the solution was dried by lyophilization.

EXAMPLE 12

104 g of soy protein powder (protein content 52%) was dissolved in 1400 cm³ of water. The solution was heated at 65° for 20 minutes, whereafter it was cooled to 50° C. The pH was adjusted with 5M Ca(OH)$_2$ to 8.5. 1.62 g of pancreatin (3% of the amount of protein) was added. The pH was allowed to drop to 7.0, whereafter hydrolysis was carried out at a pH of 7.0 for 5 hours. During the hydrolysis, the pH was adjusted with 5M Ca(OH)$_2$. The hydrolysate was ultrafiltered with a cut-off 10 000 membrane, the permeate was recovered and concentrated to have a dry solids content of 20%.

EXAMPLE 13

38 cm³ of protein hydrolysate prepared in accordance with Example 12 was measured. The pH of the solution was adjusted with 30% HCl to the value 6.8, and the solution was pumped into a 180 cm³ XAD-16 adsorption resin column at a linear flow rate of 0.9 m/h at a temperature of 65°. After the feeding of the protein hydrolysate solution batch the column was eluted with water at the same flow rate.

The protein yield was about 55%; 0.3% of the protein was phenylalanine (Table 4). The product had a pleasant taste and was not at all bitter.

TABLE 4

Amino acid composition (%) of soy protein and
PKU protein prepared from soy protein

| | Soy protein (% of protein) | PKU protein (% of protein) |
|---|---|---|
| Asp | 12.3 | 12.9 |
| Thr | 4.2 | 4.3 |
| Ser | 5.4 | 6.0 |
| Glu | 20.9 | 22.9 |
| Gly | 4.5 | 3.7 |
| Ala | 4.6 | 6.1 |
| Val | 4.8 | 4.9 |
| Cys | 1.1 | 0.3 |
| Met | 1.2 | 0.8 |
| Ile | 4.7 | 2.5 |
| Leu | 7.7 | 3.5 |
| Tyr | 2.8 | 4.2 |
| Phe | 5.0 | 0.3 |
| Lys | 6.6 | 10.3 |
| His | 2.8 | 2.3 |
| Arg | 6.8 | 11.1 |
| Pro | 4.8 | 2.0 |
| Tot | 100.0 | 100.0 |

EXAMPLE 14

In a taste comparison of PK AID III, pancreatin hydrolysate and resin-treated pancreatin hydrolysate, test participants (six persons) gave points from 0 to 3 according to the following scale:

0=no bitter taste

1=slightly bitter taste

2=clearly bitter taste

3=very bitter taste

The average of the points for the PKU protein prepared by the method described in the application was 0.2, that of PK AID III was 1.8 and that of enzyme-treated protein 3.0. In the opinion of all of the participants, the PKU protein prepared by the method described in the application was clearly the least bitter, in the opinion of five participants not at all bitter.

We claim:

1. A method for removing phenylalanine from a proteinaceous composition, said method comprising the steps of:

a) degrading enzymatically protein in a proteinaceous composition with a proteolytic enzyme into a protein hydrolysate having a degree of hydrolysis of 30 to 60%, b) ultrafiltering the protein hydrolysate thus obtained to remove non-degraded protein and recovering a permeate solution, c) passing the recovered permeate solution through a hydrophobic polystyrene-based adsorption resin at a pH from 2 to 10, at a linear flow rate of 0.1 to 1.3 m/h and at a temperature of 5° to 65° C. to absorb phenylalanine from the composition into the resin, d) eluting the resin with water at a linear flow rate of 0.1 to 1.3 m/h to form an eluate, e) recovering from the eluate a proteinaceous composition containing fraction from which phenylalanine has been substantially removed, and f) concentrating the recovered fraction to a dry solids content of at least 70% by weight.

2. The method of claim 1, wherein the proteinaceous composition is whey protein.

3. The method of claim 1, wherein the proteinaceous composition is soy protein.

4. The method of claim 1, wherein the proteolytic enzyme is pancreatin.

5. The method of claim 4, wherein the amount of pancreatin is about 3% by weight based on the amount of protein.

6. The method of claim 1, further comprising the steps of concentrating the permeate solution recovered in step b), drying the concentrated permeate solution to form a powder and dissolving the powder in hot water to form said permeate solution used in step c).

7. The method of claim 1, further comprising the step of adjusting the pH of the recovered permeate solution of step b) to a pH range of from 6.5 to 7.0.

8. The method of claim 1, wherein the permeate solution passed through the adsorption resin has a pH of from 6.5 to 7.0 and the temperature in step c) is from 30° to 65° C.

9. The method of claim 1, wherein the permeate solution passed through the adsorption resin has a pH of from 3 to 4 and the temperature in step c) is from 30° to 65° C.

10. The method of claim 9, further comprising the step of removing salts by electrodialysis from the fraction obtained in step e) before step f).

11. The method of claim 1, comprising concentrating the recovered fraction in step f) to a dry solids content of from 70 to 80% by weight and then drying the concentrate of step f).

12. A non-bitter protein hydrolysate from which phenylalanine has been substantially removed produced by a method comprising the steps of:

a) degrading enzymatically protein in a proteinaceous composition with a proteolytic enzyme into a protein hydrolysate having a degree of hydrolysis of 30 to 60%, b) ultrafiltering the protein hydrolysate thus obtained to remove non-degraded protein and recovering a permeate solution, c) passing the recovered permeate solution through a hydrophobic polystyrene-based adsorption resin at a pH from 2 to 10, at a linear flow rate of 0.1 to 1.3 m/h and at a temperature of 5° to 65° C. to absorb phenylalanine from the composition into the resin, d) eluting the resin with water at a linear flow rate of 0.1 to 1.3 m/h to form an eluate, e) recovering from the eluate a proteinaceous composition containing fraction from which phenylalanine has been substantially removed, and f) concentrating the recovered fraction to a dry solids content of at least 70% by weight.

13. The non-bitter protein hydrolysate of claim 12, wherein in step c) the permeate solution has a pH of from 6.5 to 7.0, and the temperature is from 30° to 65° C.

14. A method for treating a patient suffering from phenylketonuria which comprises administering to a patient in need thereof an effective amount of a non-bitter protein hydrolysate of claim 13 from which phenylalanine has been substantially removed.

15. The non-bitter protein hydrolysate of claim 12, in which the concentrate of step f) has been dried.

16. A method for treating a patient suffering from phenylketonuria which comprises administering to a patient in need thereof an effective amount of a non-bitter protein hydrolysate of claim 12 from which phenylalanine has been substantially removed.

* * * * *